(12) United States Patent
Ayers et al.

(10) Patent No.: US 10,172,304 B2
(45) Date of Patent: Jan. 8, 2019

(54) MICROALGAE-BASED SOIL INOCULATING SYSTEM AND METHODS OF USE

(71) Applicant: NFusion Technologies, LLC, Phoenix, AZ (US)

(72) Inventors: Andrew D. Ayers, Clay Springs, AZ (US); Mark R. Edwards, Tempe, AZ (US)

(73) Assignee: NFusion Technologies, LLC, Phoenix, AZ (US)

( * ) Notice: Subject to any disclaimer, the term of this patent is extended or adjusted under 35 U.S.C. 154(b) by 311 days.

(21) Appl. No.: 14/069,932

(22) Filed: Nov. 1, 2013

(65) Prior Publication Data

US 2014/0298717 A1   Oct. 9, 2014

Related U.S. Application Data

(63) Continuation of application No. PCT/US2012/036293, filed on May 3, 2012.

(60) Provisional application No. 61/481,998, filed on May 3, 2011.

(51) Int. Cl.

| | |
|---|---|
| *A01G 33/00* | (2006.01) |
| *C05D 9/02* | (2006.01) |
| *C09K 17/14* | (2006.01) |
| *C12N 1/12* | (2006.01) |
| *C12M 1/00* | (2006.01) |
| *C12M 1/12* | (2006.01) |
| *C05F 11/08* | (2006.01) |

(52) U.S. Cl.
CPC .............. *A01G 33/00* (2013.01); *C05D 9/02* (2013.01); *C05F 11/08* (2013.01); *C12M 21/02* (2013.01); *C12M 23/52* (2013.01); *C12M 29/04* (2013.01); *C12M 37/00* (2013.01); *C12M 43/00* (2013.01); *C12N 1/12* (2013.01)

(58) Field of Classification Search
CPC ...... C12M 21/02; C12M 23/18; C12M 31/10; A01G 33/00; C12N 1/12; Y02W 10/37; Y10S 435/946; C02F 3/32
USPC .......................................................... 47/1.4
See application file for complete search history.

(56) References Cited

U.S. PATENT DOCUMENTS

| | | | | |
|---|---|---|---|---|
| 5,947,057 | A * | 9/1999 | Perez ..................... | A01K 61/00 119/211 |
| 6,593,299 | B1 * | 7/2003 | Bennett .................. | A01N 63/02 424/408 |
| 7,682,821 | B2 * | 3/2010 | Woods ................... | C12M 21/02 126/569 |
| 2005/0061737 | A1 * | 3/2005 | Linden ................... | A01K 63/04 210/602 |
| 2009/0081743 | A1 * | 3/2009 | Hazelbeck ............. | C12M 21/02 435/157 |

(Continued)

*Primary Examiner* — Son T Nguyen
(74) *Attorney, Agent, or Firm* — The Noblitt Group, PLLC

(57) ABSTRACT

A system for inoculating soil with microalgae is provided. The system is portable and can be used with many different water sources to culture microalgae and form an inoculate that is added to irrigation water used for watering crops. The system provides improved crop production metrics as compared to crops grown without the microalgae-based inoculation system. The system can be integrated into existing irrigation systems to add macronutrients and micronutrients into the water, thereby providing highly bioavailable nutrients to crops.

28 Claims, 10 Drawing Sheets

(56) References Cited

U.S. PATENT DOCUMENTS

2010/0151558 A1\* 6/2010 Alianell ................ C12M 21/02
435/257.3
2010/0242355 A1\* 9/2010 Blotsky ................ A01C 21/00
47/1.4

\* cited by examiner

MICROALGAE-BASED SOIL INOCULATING SYSTEM AND METHODS OF USE

CROSS-REFERENCE TO EARLIER-FILED APPLICATION

This application claims the benefit of U.S. Provisional Appl. No. 61/481,998, filed May 3, 2011, and PCT Application No. PCT/US2012/36,293, filed May 3, 2012, the entire disclosures of which are hereby incorporated by reference.

FIELD OF THE INVENTION

The present invention concerns a soil inoculating system and method of use. The invention provides a microalgae-based soil inoculating system that delivers targeted nutrients and other growth factors from algae and microflora attracted to microalgae, whereby nutrients, growth factors, and water are immediately bioavailable to crops. This algae-based system improves soil structure, crop strength and crop yields. The microalgae can be delivered to crops by irrigation water or sprayer.

BACKGROUND OF THE INVENTION

The surface or ground water used for irrigation in agricultural applications generally has low macro- and micro-nutrient content. The usual approach to enrichment of ground water for agricultural use is addition of chemical fertilizers. Chemical fertilizers create a high demand for increasingly expensive chemical raw materials and have an overall negative impact upon the environment. Chemical fertilizers applied to fields must first be broken down by soil microorganisms into bioavailable form before the crops can absorb them. Algae can break down chemical fertilizers in the soil and water and deliver those nutrients in immediately bioavailable form to the crop. Additionally, the microorganisms which are fed by the algae and the products that the algae produce break down the organic matter in the soil thereby releasing these nutrients to be absorbed by the crops.

Algae in the soil surface layers function autotrophically as green plants, utilizing their photosynthetic capabilities to convert carbon dioxide, nutrients, and inorganic nitrogen into cell substance by means of energy derived from sunlight. Soil algae are divided into Chlorophyta or green algae, Cyanophyta or blue-green algae, Bacillariophyta or diatoms, and Xanthophyta or yellow-green algae. Blue-green algae are prokaryotic, and many, but not all, species fix nitrogen. Green algae are eukaryotic and do not fix nitrogen. Some species of green or blue-green algae are unicellular and others are filamentous. Although algae usually reproduce asexually by cell fission, they types can also reproduce sexually.

Certain photosynthetic microorganisms, especially algae, have been found to help control erosion, improve moisture retention, enhance soil aggregation, provide nutrients and organic matter to the soil, and reduce non sodium and chloride salinity. Algae cultures can be applied to the soil easily, for example, by mixing with water delivering the suspension to the soil in irrigation or sprayer. Algae can also be grown at the same time as the cash crop, with minimal competition for nutrients, space, sunlight, or moisture.

Algae, such as microalgae, have been added to soil in order to improve soil aggregation (U.S. Pat. No. 4,774,186) and to serve as a cover crop, which improves the soil for a cash crop, such as red clover. U.S. Pat. No. 3,969,844 discloses a method of treating soil with flocculent-producing algae and supplemental nutrients as a means for soil aggregation.

In addition to being used to improve soil aggregation, algae have been used to fix nitrogen. In particular, certain blue-green algae have been used in flooded rice fields for this purpose. The rice field ecosystem is a favorable environment for the growth of blue-green algae and that nitrogen fixation by blue-green algae plays a vital role in the buildup and maintenance of soil fertility in such fields. Release of nutrients through microbial decomposition after the death of the algae appears to be the principle means by which nitrogen is made available to the rice. Roger, P. A. and Kulasooriya, S. A., Blue-Green Algae and Rice (Manila: The International Rice Research Institute, 1980), pgs. 49-50, hereinafter Roger and Kulasooriya. The entire focus of Roger and Kulasooriya is on the use of blue-green algae for nitrogen fixation in flooded rice fields. In fact, they report that the use of the algae seems to have little effect on the physical properties of the soil, although it may improve soil aggregation. (Ibid, p. 7)

U.S. Pat. No. 6,083,293 discloses a method of enhancing crop production by applying a solution containing algae extract component, humus extract, nitrogen urea, and a yeast/molasses combination component to the crop. The inclusion of algae in a hydroculture crop production system (U.S. Pat. No. 5,121,708) has been disclosed.

U.S. Pat. No. 7,048,010 discloses that the presence of algae in an irrigation system is undesirable. Even so, the treatment of nutrient-rich water, i.e. waster water, with algae for removing nitrogen-containing and phosphorous-containing compounds from the water has been reported using a packaged algae filter having a medium for supporting algae growth and an artificial light source (U.S. Pat. No. 5,670,046) or using a bed of algae immobilized on a surface over which waste water flows to remove pollutants therein (U.S. Pat. No. 5,573,669) or using algae-containing tanks to treat water and remove pollutants (U.S. Pat. No. 5,389,257). Algae immobilized onto sheets have been suggested for use as a nutrient source for agricultural applications (U.S. Pat. No. 4,950,601). Algae have also been used to treat wastewater to form substantially purified effluent streams (U.S. Pat. No. 6,465,240).

Algae cultivation systems have been disclosed in U.S. Pat. No. 8,033,047 to Rasmussen et al., U.S. Pat. No. 8,083,836 to Wright et al., U.S. Pat. No. 8,092,685 to Gonzalez et al., U.S. Pat. No. 8,017,377 to Much, U.S. Pat. No. 7,985,338 to Chong et al., U.S. Pat. No. 7,977,085 to Rispoli et al., U.S. Pat. No. 7,977,076 to Oyler, U.S. Pat. No. 7,950,181 to McCall, U.S. Pat. No. 7,905,049 to Erd et al., U.S. Pat. No. 7,895,790 to Lin, U.S. Pat. No. 7,833,782 to Shvabsky et al., U.S. Pat. No. 7,776,211 to Limcaco, U.S. Pat. No. 7,736,508 to Limcaco, U.S. Pat. No. 7,585,898 to Thothathri, U.S. Pat. No. 5,441,877 to Chiaffredo et al., U.S. Pat. No. 5,137,828 to Robinson et al., U.S. Pat. No. 4,966,713 to Keys et al., U.S. Pat. No. 4,235,043 to Harasawa et al., U.S. Pat. No. 5,951,875 to Kanel et al., U.S. Pat. No. 6,000,551 to Kanel et al., U.S. Pat. No. 6,156,561 to Kodo et al., U.S. Pat. No. 6,416,993 to Wexler et al., U.S. Pat. No. 6,465,240 to Wexler et al., U.S. Pat. No. 6,524,486 to Borodyanski et al., U.S. Pat. No. 6,673,592 to Wang et al., U.S. Pat. No. 6,986,323 to Ayers, U.S. Pub. 20120036767 to Larach, U.S. Pub. 20120034679 to Falber, U.S. Pub. 20110307976 to Ploechinger, 20110306121 to Chou, U.S. Pub. 20110294196, U.S. Pub. 20110269219 to Holland, U.S. Pub. 20110258915 to Subhadra, U.S. Pub. 20110281339 to Riley, U.S. Pub. 20110258920 to Licamele, U.S. Pub.

20110245552 to Hassan, U.S. Pub. 20110177550 to McMurran, U.S. Pub. 20110165662, U.S. Pub. 20110122645 to Donham, U.S. Pub. 20110117638 to Veres, U.S. Pub. 20110092726 to Clarke, U.S. Pub. 20110081706 to Schlesinger, U.S. Pub. 20110076747 to Cloud, U.S. Pub. 20110065165 to Takebe, U.S. Pub. 20110045564 to Dhamwichukorn, U.S. Pub. 20110016773 to Nichols, U.S. Pub. 20100303957, U.S. Pub. 20100287829 to Bussell, U.S. Pub. 20100279389 to Ziller, U.S. Pub. 20100267125 to Erb, U.S. Pub. 20100267122 to Chinnasamy, U.S. Pub. 20100255569 to Camarate de Albuquerque Maranhao, U.S. Pub. 20100236135 to Kleinberger, U.S. Pub. 20100216203 to Trent, U.S. Pub. 20100170149 to Keeler, U.S. Pub. 20100162620 to McCaffrey, U.S. Pub. 20100099170 to Aswani, U.S. Pub. 20100034050 to Erb, U.S. Pub. 20100028976 to Hu, U.S. Pub. 20090305389 to Willson, U.S. Pub. 20090215155 to Cloud, U.S. Pub. 20090211150 to Wu, U.S. Pub. 20090188290 to Marler, U.S. Pub. 20090162919 to Radaelli, and U.S. Pub. 20090151240 to Kayama. None of these systems suggest or disclose the present system and its methods of use.

SUMMARY OF THE INVENTION

The present invention provides a microalgae-based soil and seed inoculating system useful for enhancing the nutrient content of water used in agricultural applications. The system converts nutrient-poor water to nutrient-rich water by cultivating microalgae in, and adding microalgae-derived nutrients to, the water to form nutrient water used to inoculate soil. The nutrient water comprises microalgae, and algae-derived nutrients, that are immediately bioavailable and beneficial to soil and plants. The nutrient infused water can be used to irrigate crops and thereby enhance their production such as by increasing crop, seed, grain and/or fruit yield. The portable system inoculates the soil with microalgae carried to the field by irrigation. Farms that depend on and do not have the irrigation delivery system may inoculate the soil with algal slurry by field or aerial sprayer. The algae can be forced into the soil with additional water.

The portable system can be used to produce microalgae on-site for use as a nutrient delivery system, organic biofertilizer and biological soil conditioner. The system can reduce the farmer's costs for chemical fertilizer and mitigate erosion and ecological pollution. The system enables the farmer to reduce dependence on freshwater consumption, fossil fuels, fertilizers and agricultural chemicals while reducing air, soil and water pollution. The system is intended to enhance crop productivity, enable the rapid transformation to organic production and minimize waste and ecological pollution.

The system is intended to deliver micronutrients embedded in algae that are free of toxic heavy metals and are bioavailable just in time for crop needs. At the same time, crops are benefiting from high-value nutrients delivered just when they are most needed. Algae condition the soil to improve porosity, water retention and soil organics. Soils conditioned with algae exhibit accelerated and extended root development, require less energy in tillage and are significantly more resistant to erosion.

If chemical fertilizers are included in a water source, the algae can convert a portion of the chemical fertilizers into a bioavailable form that enables plants to immediately use the nutrients, which minimizes waste and eliminates pollution. The system can deliver specific nutrients targeted for each stage of the life cycle of a crop. Enhanced nutrient delivery increases yield and produce quality significantly.

One aspect of the invention provides a portable microalgae-based soil inoculating system comprising: a) at least one ozone source adapted to add ozone to a water source to form ozone-treated water; b) at least one solids filter adapted to remove solids from incoming water to form filtered water; c) at least one carbon filter adapted to remove ozone from filtered water to form carbon filter-treated water; d) at least one UV light system to further sterilize the water and remove excess ozone which may pass through the carbon filter; e) at least one microalgae-nutrient feed source adapted to add algae-nutrient feed to carbon filter-treated water to form feed water f) at least one bioreactor adapted for receiving the feed water and cultivating microalgae and forming a microalgae-containing inoculant effluent, when a microalgae is present therein; g) at least one blower comprising a first outlet adapted to provide air to the at least one oxygen concentrator or directly to the at least one ozone source and a second outlet adapted to provide air to the at least one bioreactor; and h) at least one carbon dioxide source adapted to add carbon dioxide to air provided to the at least one bioreactor or directly to the at least one bioreactor.

Some embodiments of the invention include those wherein: 1) the system further comprises at least one water conduit conductively connecting the at least one solids filter, at least one carbon filter, at least one UV light system, at least one microalgae-nutrient feed source, and at least one bioreactor; 2) the water source comprises at least one tank adapted to temporarily hold water; 3) the system further comprises at least one water reservoir; 4) at least one oxygen concentrator; 5) the at least one ozone source is an ozone generator or a tank containing ozone; 6) the at least one solids filter is a mechanical filter; 7) the at least one carbon filter comprises activated carbon; 8) at least one UV light system; 9) the system further comprises at least one light source adapted to expose microalgae to light; 10) the at least one carbon dioxide source is a tank containing carbon dioxide gas, a carbon dioxide generator, or carbon dioxide-sequestering means for sequestering and temporarily storing atmospheric carbon dioxide; 11) one or more of the solids filter, carbon filter, UV light system, and/or bioreactor is a flow-through apparatus; 12) the system further comprises at least one pump for forcing water through the at least one water conduit; 13) the system further comprises at least one air conduit conductively connecting the blower, the at least one ozone source and/or the at least one carbon dioxide source to the at least one bioreactor; 14) the system further comprises at least one air conduit conductively connecting the blower, the at least one ozone source, the at least one carbon dioxide source and the at least one bioreactor; 15) the system comprises at least two different microalgae-nutrient feed sources; 16) the system further comprises a flow-through mixer adapted to receive water and ozone, mix the two components and provide ozone-treated water; 17) at least one microalgae-nutrient feed source comprises carbon dioxide, one or more macro-fertilizers, and one or more micro-fertilizers. Suitable macro-nutrients useful for aiding algal growth include nitrogen, phosphorus, potassium, carbon, calcium, magnesium, and silicon (if a diatom is to be cultured). Suitable micronutrients, those nutrients required by plants and animals in very small quantities, comprise iron, manganese, copper, zinc, cobalt, molybdenum, chromium, selenium, vitamin B12, biotin and thiamine and other trace elements.

Some embodiments of the invention provide a portable microalgae-culture system comprising: at least one oxygen concentrator; at least one ozone source; at least one flow-through water filter comprising a particulate filter an activated carbon-containing filtration medium and a UV light system; at least one algae-nutrient feed source; at least one flow-through bioreactor adapted to temporarily retain microalgae and water; at least one carbon dioxide source; at least one water conduit; at least one air conduit; at least one air blower or air pump; at least one water pump; and at least one portable body onto which other components of the system are mounted; wherein the blower or air pump is adapted to force air through at least one air conduit to the at least one oxygen source and through at least one ozone source and through at least one other air conduit; the ozone source is adapted to convert oxygen in the air or from an oxygen concentrator to ozone; the at least one water pump is adapted to circulate water through the at least one water conduit; the at least one water filter is, optionally, adapted to receive ozone-treated water and provide filtered water to at least one water conduit; the at least one algae-nutrient feed source is adapted to add at least one algae-nutrient to the filtered water and thereby provide a feed water; and the at least one carbon dioxide source is adapted to add carbon dioxide to air in the at least one other air conduit.

Some embodiments of the invention include those wherein: 1) the system further comprises at least one water pump for flowing water through the at least one water conduit; 2) the system further comprises at least one tank adapted to receive feed water and hold algae; 3) the system comprises at least two different algae-nutrient feed sources; 4) the system further comprises a water source; 5) the system further comprises a contact tank adapted to receive water and ozone, mix the two components and provide ozone-treated water; 6) the system comprises plural bioreactors; 7) the system further comprises at least one artificial light source; 8) the system further comprises at least one portable body onto which other components of the system are mounted; 9) at least one bioreactor or plural bioreactors comprise(s) a light-permeable wall; 10) the system further comprises conduits (plumbing) conductively connected to one or more cultivation containers; 11) the system further comprises a cleaning system for conduits, reservoirs, and/or containers; 12) the system further comprises one or more monitors that assess culture properties and/or performance.

Another aspect of the invention provides a method of growing a crop comprising: a) providing an irrigation-water source; b) conducting irrigation-water through a first microalgae culture system to form a first inoculant comprising first microalgae; c) irrigating the crop one or more times with the first inoculant during a first life-cycle phase of the crop; then, d) conducting irrigation-water through a different second microalgae culture system to form a different second inoculant comprising different second microalgae; e) irrigating the crop one or more times with the second inoculant during a second life-cycle phase of the crop.

Another aspect of the invention provides a method of eliminating, killing or rendering non-viable unwanted microbes, nematodes, bugs or insects from soil, the method comprising: a) providing an irrigation-water source; b) conducting irrigation-water through a first microalgae culture system to form a first inoculant comprising first microalgae comprising one or more biotoxins that are toxic to a soil microbe, nematode; bug or insect c) irrigating the soil containing unwanted microbe, nematode, bug or insect one or more times with the first inoculant, thereby eliminating, killing or rendering non-viable the unwanted microbe, nematode, bug or insect.

In some embodiments, the microalgae are blue-green or green algae but other types of algae can also be employed. Any unicellular microalgae named herein as being adapted for growth in fresh water will be suitable for use in the system and method of the invention. Exemplary species include, by way of example and without limitation, microalgae such as *Muriellopsis* spp., *Chlorella fusca, Chlorella zofingiensis, Chlorella* spp., *Haematococcus pluvialis, Chlorococcum citriforme, Neospongiococcum gelatinosum, Chlorella stigmataphora, Chlorella vulgaris, Chlorella pyrenoidosa, Chlamydomonas mexicana, Scenedesmus obliquus, Scenedesmus braziliensis, Nitzschia palea*. Unicellular algae from the Divisions Chlorophycophyta, Phaeophycophyta, Chrysophycophyta, Cyanophycophyta, Cryptophycophyta, and Pyrrhophycophyta, which are adaptable to fresh water as a growth medium, are all suitable for use in the present invention. Some embodiments of the invention include those wherein: a) the microalgae is selected from the group consisting of cyanobacteria genera, *Nostoc, Scytonema* and *Hapalosiphon*; b) the biotoxin (toxin) produced by the microalgae is selected from the group consisting of microcystins or plant hormone; c) the microcystin inhibits growth, photosynthesis, and creates oxidative stress in *Lemna*; d) the plant hormone is a plant growth regulator selected from the group consisting of auxins, cytokinins and gibberellins.

Some embodiments of invention include those wherein: 1) the irrigation-water source is freshwater, e.g. river water, stream water, creek water, lake water, rain water, well water, pond water; or wastewater, e.g. from farm, wetlands, industrial or municipal source; 2) the first microalgae is blue-green microalgae; 3) the second microalgae is green microalgae; 4) the first life-cycle phase comprises the vegetative stage, e.g. germination, main shoot growth, auxiliary shoot growth; 5) the second life-cycle phase comprises the reproductive stage, e.g. flowering, fruit formation, or ripening; 6) the method further comprises repeating steps d) and e) with a different third microalgae during a third life-cycle phase of the crop; 7) the third life-cycle phase comprises senescence and/or dormancy; 8) the method further comprises providing first at least one microalgae-nutrient feed source for use with the first microalgae; 9) the method further comprises providing a different second at least one microalgae-nutrient feed source for use with the second microalgae; 10) the method is carried out with a portable microalgae-based soil inoculating system as described herein; 11) the first microalgae culture system differs from the second microalgae culture system in the species of microalgae and optionally in the content of the microalgae feed source; and/or 12) any number of cultures may be used to maximize delivery of plant-needed nutrients just in time.

Some embodiments of the invention further comprise a telemetry system that assists with remote monitoring and/or controlling operation of one or more components of the system of the invention.

In some embodiments, the blue-green microalgae provide a source of nitrogen and/or fixes nitrogen from the atmosphere into soil.

The invention includes all combinations of the aspects, embodiments and sub-embodiments of the invention disclosed herein.

BRIEF DESCRIPTION OF THE FIGURES

The following figures form part of the present description and describe exemplary embodiments of the claimed invention. The skilled artisan will, in light of these figures and the description herein, be able to practice the invention without undue experimentation.

DETAILED DESCRIPTION OF THE INVENTION

Figure 1:
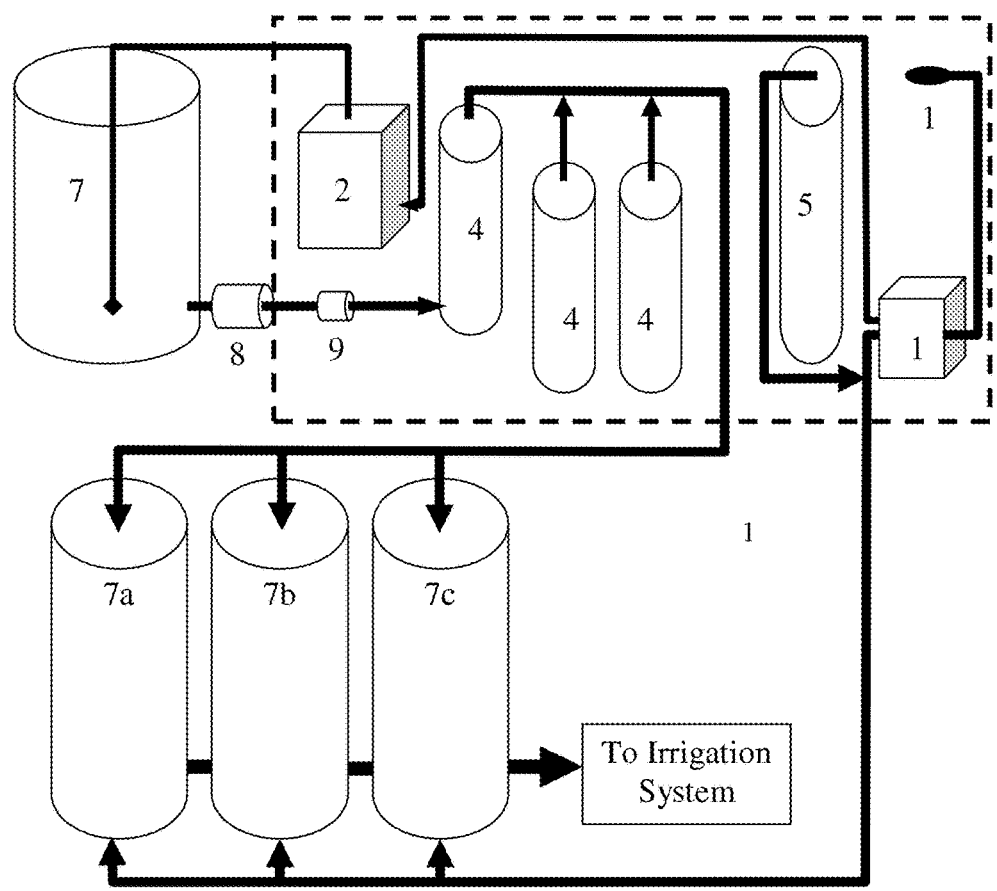
FIG. 1 depicts a first embodiment of the microalgae-based soil inoculating system of the invention.

The system delivers a full range of micronutrients in microalgae to soil into which the microalgae containing water (effluent) is inoculated thereby making the micronutrients immediately bioavailable to crops grown in the soil. The system of the invention is placed within an irrigation system between the water source and the water ports, through which irrigation water is applied to crops. The system produces biofertilizers that are immediately bioavailable to crop, such that negligible runoff pollution occurs. Inorganic agricultural chemicals can be used more efficiently after being converted into a bioavailable form by the algae; therefore, the amount of chemicals needed is reduced.

The system can be used to build soil organics with nutrient-rich algae biomass to recover depleted (nutrient poor) soils. The system can facilitate and accelerate the transformation of a chemicals-based farm to an organic farm. The system delivers to the soil microalgae that dissolve soil carbonates, build polysaccharide sheaths in the topsoil and improve soil porosity up to 500% or more. The system also provides for use of specific algal biotoxins in place of conventional chemical fungicides and other chemical poisons/toxins to manage nematodes and other harmful pests.

The microalgae in the bioreactor propagates so an initial microalgae inoculant placed into the bioreactor can conceivably provide an endless supply of microalgae provided sufficient microalgae feed and water is loaded into the bioreactor and a sufficient amount of microalgae biomass is removed from the bioreactor periodically so as to keep the conditions within the bioreactor suitable for microalgae culture.

The system and its method of use can improve overall crop production 5 to 30% or higher as compared to untreated crops. It can improve the texture, taste, size, nutrient content and/or yield of a crop as compared to untreated crop. In terms of agriculture use, the system can reduce total energy consumption, reduce ecological pollution, reduce greenhouse gas emission, increase bioavailability of micronutrients and macronutrients, reduce the use of chemical fertilizers, reduce overall crop production cost, reduce tillage cost, reduce need for and use of fungicides, herbicides and/or pesticides, reduce soil compaction, improve soil porosity, increase microbial content of soil, increase organics content of soil, reduce the amount of irrigation water needed to grow a crop, reduce the occurrence of over fertilization, reduce run-off and soil erosion, improve plant characteristics and/or improve water/moisture retention by soil, all as compared to untreated crop.

The system can be used to reduce or eliminate the buildup of carbonates in irrigation equipment by flowing microalgae-containing water through the irrigation equipment. It can also be used to reduce or eliminate buildup of carbonates in soil by inoculating the soil with microalgae-containing water.

The method of inoculating soil can comprise: obtaining a sample of soil from a target geographic location; isolating a robust indigenous microalgae species from the sample; culturing the microalgae to form a first inoculate; inoculating a portable microalgae-based soil inoculating system with the first inoculate; culturing the microalgae in the inoculating system to form a second inoculate; and inoculating soil of the target geographic location one or more times with the second inoculate. In some embodiments, the indigenous microalgae species will possess properties that make it optimal for growth under the environmental conditions of the target geographic location. In some embodiments, algae from non-indigenous locations or algal collections may be used to inoculate the soil of the target geographic location in order to maximize specific bioavailable compounds.

The system of the invention can employ various different types of water as the water source: wastewater, well water, lake water, creek water, pond water, rainwater, river water and freshwater. Since the water is intended for crop growth, it is preferred that the water source has low salinity and is free from heavy metals. After exiting the micro-algae inoculating system, the inoculate-containing water can be delivered to a crop by any conventional irrigation means or system used in agriculture, for example, by flood, sprinklers or drip type of irrigation systems or by sprayer or aerial application. If applied by sprayer or aerial application the treatment should be followed by sufficient water to drive the algae into the soil.

The method of the invention provides for continuous, semicontinuous, repeated or periodic treatment of soil with microalgae-containing inoculate. For example, the soil can be treated with microalgae-containing inoculate daily, every other day, every third day, semi-weekly, every fourth day, every fifth day, every sixth day, weekly, biweekly, every third week, every fourth week, monthly, bimonthly, quarterly, trimesterly, semiannually, annually or a combination thereof. In some embodiments, the soil can be treated with water not containing the microalgae and then with water containing microalgae inoculate, or vice versa. The invention includes dilute, semi-concentrated and concentrated algal cultures with a single algal species or two or more different algal species. Although it is optional, additional crop nutrients (macronutrients and/or micronutrients), aside from microalgae feed, can be included in the irrigation water. For example, nutrients such as calcium may be incorporated into the algal species for transport and uptake by the crops. The following table includes exemplary macronutrients and micronutrients.

| Macronutrients | | Micronutrients | |
|---|---|---|---|
| Nitrogen | (N) | Boron | (B) |
| Phosphorus | (P) | Sulfur | (S) |
| Potassium | (K) | Copper | (Cu) |
| Carbon | (C) | Chloride | (Cl) |
| Oxygen | (O) | Iron | (Fe) |
| Magnesium | (Mg) | Molybdenum | (Mo) |
| Calcium | (Ca) | Manganese | (Mn) |
| | | Nickel | (Ni) |
| | | Zinc | (Zn) |
| | | Selenium | (Se) |
| | | Chromium | (Cr) |
| | | Cobalt | (Co) |
| | | Biotin | |
| | | Thiamin | |
| | | Vitamin B12 | |

Algae operate symbiotically with other organisms, both microorganisms and macroorganisms. While the primary object of this application focuses on culturing algae, culturing algae in a diverse community of multiple microorganisms may offer useful solutions. Nitrogen-fixing microbes, called diazotrophs, fall into two main groups, free-living and symbiotic. Aerobic diazotrophs, of which there are over 50 genera, including *Azotobacter*, methane-oxidizing bacteria, and cyanobacteria, require oxygen for growth and fix nitrogen into soil when oxygen is present. *Azotobacter*, some related bacteria, and some cyanobacteria fix nitrogen in ordinary air, but most members of this group fix nitrogen only when the oxygen concentration is low. *Aphanizomenon flosaquae* reduces acetylene and fixes nitrogen in algal cultures. Exemplary symbiotic bacteria belong to the genus *Rhizobium* such as *Bradyrhizobium* and *Sinorhizobium*, which colonize the roots of leguminous plants and stimulate the formation of nodules within which they fix nitrogen microaerobically. Green microalgae provide nitrogen, phosphorous, potassium, calcium and various other micronutrients. Accordingly, the invention includes embodiments wherein one or more microalgae are co-cultured with or are inoculated into soil along with one or more diazotrophs.

Suitable microorganisms and macroorganisms that can be co-cultured with or inoculated into soil along with the microalgae and/or algae include:

Actinomycetes—which are thread-like bacteria that look like fungi. While not as numerous as bacteria, they perform vital roles in the soil. They help decompose organic matter into humus, which slowly releases nutrients. They also produce antibiotics to fight roots diseases. The same antibiotics are used to treat human diseases. Actinomycetes create the sweet, earthy smell of biologically active soil when a field is tilled.

Bacteria—There are many different species of bacteria, each with its own role in the soil ecosystem. Bacteria break down complex molecules and enable plants to take up nutrients. Some species release N, S, P and trace elements from organic matter. Others break down soil minerals and release K, P, Mg, Ca and Fe. Other species make and release natural plant growth hormones, which stimulate root growth. A few bacteria fix N in the roots of legumes while others fix N independently of plant association. Bacteria are responsible for converting N from ammonium to nitrate and back again depending on soil conditions. Various bacteria species increase the solubility of nutrients, improve soil structure, fight root diseases, and detoxify soil.

Fungi—Some species appear as thread-like colonies, while others are one-celled yeasts. Slime molds and mushrooms are also fungi. Many fungi aid plants by breaking down organic matter or by releasing nutrients from soil minerals. Fungi are generally early to colonize larger pieces of organic matter and begin the decomposition process. Some fungi produce plant hormones, while others produce antibiotics including penicillin. Several fungi species trap harmful plant-parasitic nematodes.

Mycorrhizae—a group of fungi lives either on or in plant roots and act to extend the reach of root hairs into the soil. Mycorrhizae increase the uptake of water and nutrients especially in less fertile soils. Roots colonized by mycorrihizae are less likely to be penetrated by root-feeding nematodes since the pest cannot pierce the thick fungal network. Mycorrhizae also produce hormones and antibiotics, which enhance root growth and provide disease suppression. The fungi benefit from plant association by taking nutrients and carbohydrates from the plant roots where they live.

Nematodes—which are abundant in most soils and eat decaying plant litter, bacteria, fungi, algae, protozoa and other nematodes and speed the rate of nutrient cycling. Only a few species are harmful to plants and would be excluded from the inoculate of the invention.

Protozoa—free-living microorganisms such as amoeba that crawl or swim in the water between soil particles. Soil protozoa are predatory and feast on other microbes, including bacteria. Protozoa accelerate the cycling of N from the bacteria, making it more available to plants.

Bacteria suitable for co-culture with the microalgae and for use in the system of the invention are disclosed in U.S. Pat. No. 7,736,508 to Limcaco (Jun. 15, 2010), the relevant disclosure of which is hereby incorporated by reference.

Aside from revitalization or nutrient supplementation of soil, the system and method of invention can also be used in place of or to reduce the need for conventional herbicides, pesticides, fungicides and nematocides. For example, after harvest, an algal species with specially selected toxins may be applied to manage nematodes and other soil predators. The algae with toxins are naturally occurring and typically die out after killing the nematodes. While it is possible for algae to mutate, indigenous algae will be far more robust and quickly crowd out any remaining toxic algae. Microalgae suitable for use as pesticides include algae from the genera *Nostoc, Scytonema*, and *Hapalosiphon*. The system and methods of the invention can be used in places such as soil-based farms, parks, hydroponic farms, aquaponics, nurseries, golf-courses, sporting fields, orchards, gardens, zoos and other such places where crops or plants are grown. Additional phytotoxins obtainable from microbes are described by Duke et al. ("Chemicals from Nature for Weed Management", *Weed Science*, (2002) vol. 50, pg. 138-151). Exemplary phytotoxins include actinonin, brefeldin, carbocyclic coformycin, cerulenin cochlioquinone, coronatine, 1,4-cineole, fischerellin, fumosin, fusicoccin, gabaculin, gostatin, grandinol, hydantocidin, leptospermone, phaseolotoxin, phosphinothricin, podophyllotoxin, prehelminthosporol, pyridazocidin, quassinoid, rhizobitoxin, tagetitoxin, sorgoleone syringotoxin, tentoxin, tricolorin A, thiolactomycin and usnic acid.

A field, to which inoculate is applied, can receive sunlight during the growing season of a target crop grown on that location. Likewise, if the field is to be treated with microalgae as a pesticide, the field should receive sufficient sunlight during the treatment period in order to effectively remove or kill the pest.

The bioreactor of the invention can be adapted to receive and use natural or artificial light. As such the bioreactor must be adapted to permit exposure of microalgae to a light source. In some embodiments, the wall of the bioreactor comprises a light-permeable material to permit exposure of the microalgae to light. If an artificial light source is used, the light source can be placed within or at the exterior of the bioreactor, e.g. according to U.S. Pat. No. 8,033,047, the entire disclosure of which is hereby incorporated by reference. Alternatively, the system can comprise water conduit having through which microalgae-containing water in the bioreactor can be circulated to expose the microalgae to light. The water conduit can be adapted to employ sunlight, reflected, bent, fiber optic or artificial light.

The system of the invention can be run continuously, semi-continuously or in a batch-type operation.

The system can further comprise one or more monitors (sensors) adapted to monitor: a) growing conditions within the bioreactor; b) microalgae cell titer/cell count in the water; c) pH of the water; d) salinity of the water; e) the presence of undesired microbes in the bioreactor; f) water level; g) water pressure; h) level of microalgae nutrients; i) level of solids in the filtered water; j) the level of undesired compound(s) in the water; k) oxygen, ozone and/or $CO_2$ content in the water; l) level of nitrogen compounds in the water; m) clarity or opacity of the water; n) level of desired compound(s) in the water; o) water flow-rate; p) weed algae; q) algal predators; and/or) other contaminants.

The monitor(s) (sensor(s)) can be used to control operation of the system, such as by feedback regulation. A monitor may generate one or more signals to controllers, which control the flow of materials into and/or out of the system. For example, a microalgae cell titer monitor may send one or more signals to one or more flow controllers that the flow of source water or microalgae-containing water into and/or out of the system. A pH monitor may send one or more signals to a $CO_2$ flow controller that controls the amount of or rate at which $CO_2$ is added to the system. A water level monitor may send one or more signals to a water flow controller that controls the amount of or rate of water flow into and/or out of the system. A pH monitor may send one or more signals to an acid or base titrating unit that controls the amount of or rate of acid or base is flow into and/or out of the system. A water pressure monitor may send one or more signals to a water pressure regulator that controls the amount of or rate of water flow into and/or out of the system. An ozone monitor may send one or more signals to an ozone flow controller that controls the amount of or rate at which ozone is added to the system. A clarity monitor may send one or more signals to a water clarity controller that controls the efficiency of filtration of water in the system. A nutrient monitor may send one or more signals to a nutrient source flow controller that controls the amount of or rate at which nutrient for the microalgae is added to the system.

In order to grow, plants and microalgae need nutrients such oxygen, carbon, nitrogen, phosphorus, potassium, magnesium, sulfur, boron, copper, chloride, iron, silicon, sodium, manganese, molybdenum, zinc, cobalt, vanadium, bismuth, iodine, water, carbon dioxide, air and/or others.

The profile of macronutrients and micronutrients provided by the microalgae will depend upon the strain or species of microalgae used. Plants may require a different spectrum of micronutrients and macronutrients during the different stages of the life cycle of the plant. The invention provides a method of growing crops wherein the macronutrient and micronutrient profile of microalgae is matched with particular phases in the life cycle of a plant. A field may receive regular nutrient feedings during crop growth and development with different species used depending on the needs of the crop. For example, microalgae A provides a nutrient profile A, microalgae B provides a nutrient profile B, and a target crop requires a nutrient profile A during the early stages of growth and a nutrient profile B ring of the latter stages of growth. In such a situation, the soil in which the crop is planted will be inoculated first with microalgae A during the early stages of growth of the target crop and will be inoculated then with microalgae B during the latter stages of growth of the target crop.

Accordingly, the invention provides a method of producing a crop comprising: planting a crop into soil and inoculating the soil with a first microalgae that provides a first nutrient profile; allowing the plant to pass from a first stage of growth into a second stage of growth; and inoculating the soil with a second microalgae that provides a different second nutrient profile. In some embodiments, the first nutrient profile will be optimal for plant growth during the first stage, and the second nutrient profile will be optimal for plant growth during the second stage.

FIG. 1 depicts a first embodiment of a portable microalgae-based soil-inoculating system (1) of the invention. The system comprises a water source (7), an ozone source (2), a carbon filter (3), a UV light system, (4), a water pump (8), a solids filter (9), microalgae nutrient source (5a, 5b), bioreactors (7a, 7b, 7c), a carbon dioxide source (6), a blower/air pump (10) and various and water conduits. Air is taken from the atmosphere or a tank via the inlet (11), which optionally includes an air filter. The air passes through the air pump (10) to an ozone source (2), whereby ozone-treated air is formed and conducted into a water source (7) to form ozone-treated water. Air is also injected with a carbon dioxide source (6) to form carbon dioxide-treated air that is conducted into the bioreactors (7a-7c) or into water entering the bioreactors. The ozone treated water is filtered through a solids filter (9) a carbon filter (3) and a UV light system (4) to form filtered water to which microalgae feed is added by the microalgae feed source (5a, 5b) to form feed water, which is conducted into the bioreactor. During initial startup, the bioreactors are filled with water containing microalgae nutrients and are then inoculated with a first inoculate containing microalgae. Carbon dioxide-containing air is injected into the microalgae-containing water in the bioreactors. The water in the bioreactor is recirculated for a period of time until the microalgae cell titer/cell count has reached a target level suitable for use as an inoculant. Water from the system is then flowed into the irrigation water, to form a microalgae-containing inoculate as the effluent, which is applied to the soil. Various different operation parameters can be controlled.

One or more heaters are optionally included in the system to heat water conducted through the system and/or heat the culture medium in the bioreactor, thereby permitting culture of microalgae and use of the system even during cold weather.

A system of the invention will comprise one or more bioreactors. In some embodiments, the system comprises plural bioreactors. When plural bioreactors are present, the bioreactors can be the same or different. Likewise, the contents of the bioreactor can be the same or different. The culture medium in a bioreactor will comprise one or more types of microalgae. Some embodiments of the invention include those wherein: a) all of the microalgae are of the same type; b) two more different types of microalgae are present; and/or c) one or more bioreactors contain one or more types of microalgae, and one or more other bioreactors contain one or more other types of microalgae.

The volume of system water and its flow rate into the irrigation water is adjusted as needed to provide the appropriate level of inoculation and water penetration into the soil. For example, a 200-acre field might receive a total daily volume of 500 to 1 thousand gallons of water at a delivery rate of 21 to 42 gallons/hour. The inoculate obtained from the bioreactor can be applied to soil with or without further dilution. For example, the system can be operated such that all water used for irrigation flows through the bioreactor. Otherwise, the system can be operated such that the inoculate, the effluent of the bioreactors, is diluted with additional irrigation water prior to application to the soil.

The microalgae cell titer (the cell count) in a bioreactor fluctuates over time; therefore, the cell titer of the effluent varies as well. The titer provides important metrics regarding the unit's health and productivity. Generally, the titer in the effluent will be at least 1,000,000 cells per ml up to 10,000,000 cells per ml. The titer is also species specific, and can be higher or lower than the range stated above.

The ozone is used to destroy unwanted microbes present in the irrigation water prior to entering the bioreactor. Any organic contaminants present in the system can be removed by ozonolysis as described in U.S. Pat. Nos. 5,947,057 and 5,732,654 to Perez et al. Organic contaminants include herbicides, pesticides, and fungicides among other things. The ozone source can be a tank containing ozone, an ozone generator a combination thereof. Suitable ozone generators include the model O1 by Pacific Ozone, the Nano by Absolute Ozone, and the OZ8PC20 by Ozotech. The water is treated with ozone as required according to the quality of the water entering the system. The concentration of ozone in the water and prior to filtration through a carbon filter will vary with water quality, but have a minimum ozone level of 0.2 ppm up to a max of 0.5 ppm. It is preferable that the concentration of ozone in water entering the bioreactor is less than 0.01 ppm. Treatment of the water with ozone may be improved by employing a mixer that mixes the water and ozone.

The carbon filters and UV light systems are used to remove ozone from the irrigation water prior to entering the bioreactor. The carbon filter generally employs a minimum of 0.75 ft$^3$ of activated carbon. In some embodiments, the carbon filter and UV light systems are flow-through systems. Suitable carbon filters include the 0.75 ft$^3$ Upflow Carbon Filter System from Affordable Water (www.affordablewater.us). Suitable UV systems include the CSL Series by Aquafine, and the UVS3XX Series by UV Sciences (www.aquaneuv.com; Valencia, Calif.). A UV light system can be used to disinfect water prior to entering the bioreactor, and/or to destroy ozone, destroy chlorine or chloramines prior to entering the bioreactor. The UV light system can disinfect by inactivating or killing microorganisms in the water.

When a solids filter is present, it is used to remove solids from the irrigation water prior to entering the bioreactor. In some embodiments, the solids filter is a flow-through filter. Suitable solids and filters include the X100 bag filter from www.filterbag.com or the FV1 bag filter at www.aquatice-co.com.

Suitable carbon filters and/or solids filters include media filters, disk filters, screen filters, microporous ceramic filters, carbon-block resin filters, membrane filters, ion-exchange filters, microporous media filters, reverse osmosis filters, slow-sand filter beds, rapid-sand filter beds, cloth filters and other such filters.

The carbon dioxide is used as a carbon source for microalgae. It is added directly or indirectly to the bioreactor. The carbon dioxide source can be a tank containing carbon dioxide, a carbon dioxide generator, a carbon dioxide sequestering device that sequesters carbon dioxide from the atmosphere, or a combination thereof. Alternatively, carbon dioxide captured from air can be used, e.g. U.S. Pat. No. 8,083,836, the entire disclosure of which is hereby incorporated by reference.

Atmospheric air contains approximately 0.035-0.04% wt. of carbon dioxide. While atmospheric air can serve as a source of carbon dioxide for the microalgae, the concentration of carbon dioxide is generally too low to sustain the rapid proliferation of microalgae in the bioreactor. Accordingly, carbon dioxide is added to the air that is fed into the culture medium. The concentration of carbon dioxide in the air added to the culture medium is generally in the range of 1-3% wt, 1.5-2.5% wt., 1.8-2.2% wt. or about 2% wt.

A water pump might or might not be included in the system. When present the water pump can facilitate the flow of water through the water conduits and/or bioreactors of the system. If a water pump is not included, the pressure of the irrigation water entering the will be sufficient to drive water through the system.

An air pump or blower (the terms are used interchangeably herein) must be included in the system. The air pump can facilitate the flow of air, which may or may not include carbon dioxide or ozone, through the air conduits, water source and/or bioreactors of the system.

Many different species and strains of microalgae can be used according to the crop needs. Algae may be collected and cultivated from the field where crops are to be grown or from commercial sources. Microalgae samples can be obtained from repositories at Arizona State University, University of California at Berkeley, University of Texas at Austin, Woods Hole Oceanographic Research Institute, Scripps Institute of Oceanography or other repositories.

Different species and strains of microalgae grow best under different conditions. The culture conditions within the bioreactor will be varied according to the particular species of microalgae present in the bioreactor. Conditions for culturing many different types of microalgae can be found in The Handbook of Microalgal Culture: Biotechnology and Applied Phycology (ed. Amos Richmond, Blackwell Publishing, Oxford, U.K., 2004), Algal Culturing Techniques: A Book for All Phycologists (ed. Robert A. Andersen, Elsevier Academic Press, 2005), and Microalgae: Biotechnology and Microbiology Cambridge Studies in Biotechnology (ed. E. W. Becker. Press Syndicate of the University of Cambridge, 1994), the disclosures of which are hereby incorporated in their entirety by reference.

The size or operating capacity of each piece of equipment comprising the system can be varied as needed. For example, a portable system comprising a total bioreactor capacity of 500 gallons of culture medium can support 200 acres of land and will general require the following minimum operating capacities for the indicated components: a) ozone source-1.5 g/hr; (dry air); b) solids filter-40 g/min maximum flow with a minimum 2 ft² surface area; c) carbon filter-0.75 ft³ minimum; d) water pump-10 gal/min minimum; e) air blower/air pump-25 cfm at 60" H₂O minimum; 0 microalgae feed source-1.0×10⁶ cells/ml minimum; g) liquid carbon dioxide source-80 l/week.

Figure 2:
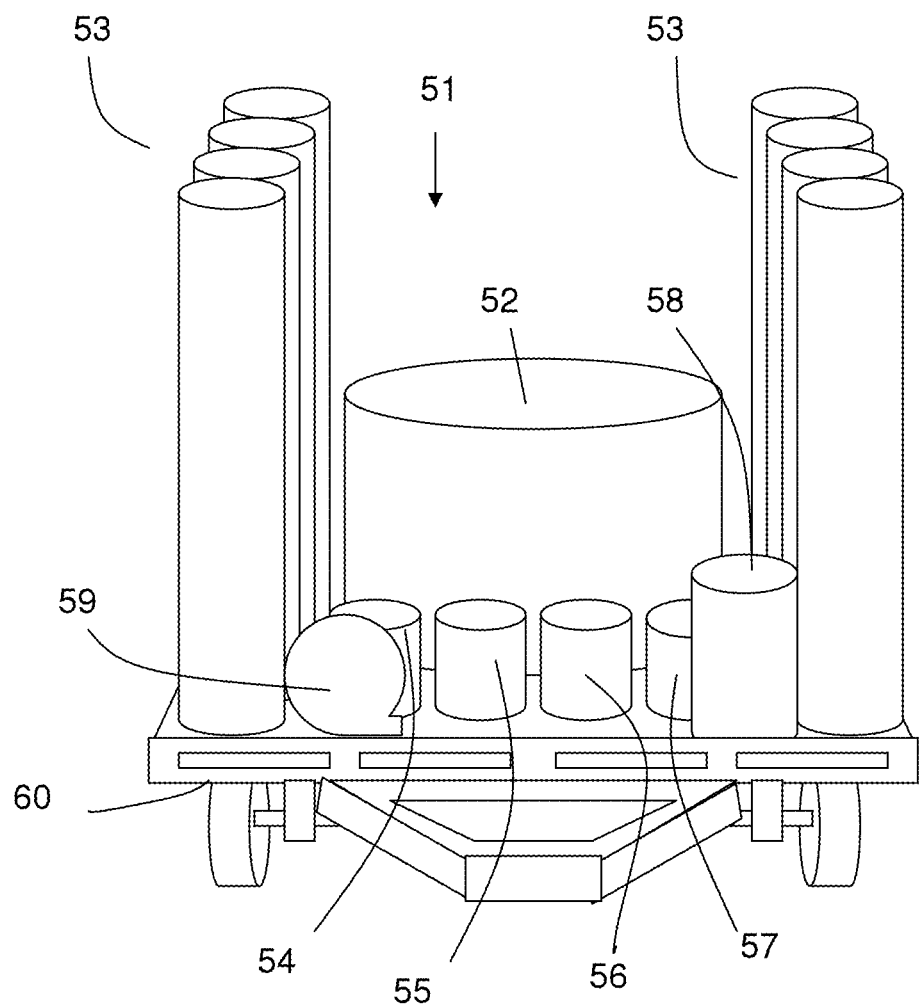
FIG. 2 depicts a front-perspective view of a second embodiment of the microalgae-based soil inoculating system of the invention.

FIG. 2 depicts another embodiment (51) of the portable system of the invention, wherein the components are mounted on a trailer. The system comprises a water tank (52), plural bioreactors (53), an ozone generator (54), a clarifier (55), a combination filter/UV light system (56), nutrient feed supply (57), CO₂ concentrator (58), a blower (59) and a trailer (60). This system has a flow-through capacity of about 0.35-0.7 gal/min and can be used to support a field in the range of 200-500 acres. The water tank receives water from the on-site water source of a farm. The system comprises eight bioreactors (500 gal total capacity), a water tank, air filter, solids filter, carbon filter, UV light system, ozone source, carbon dioxide source, microalgae nutrient source, blower and water pump (not shown). The bioreactors have light-permeable walls such that sunlight is used as the light source. The carbon dioxide and air are bubbled into the lower part of the bioreactor so the bubbles agitate the culture medium as they rise. The system optionally comprises a mechanical agitator. This system can provide a minimum of about 22 million microalgae cells per second via the effluent, assuming a water flow rate of about 0.35 gal/min and can even provide 500 MM to 1000 MM or higher cells per second.

Figure 3:
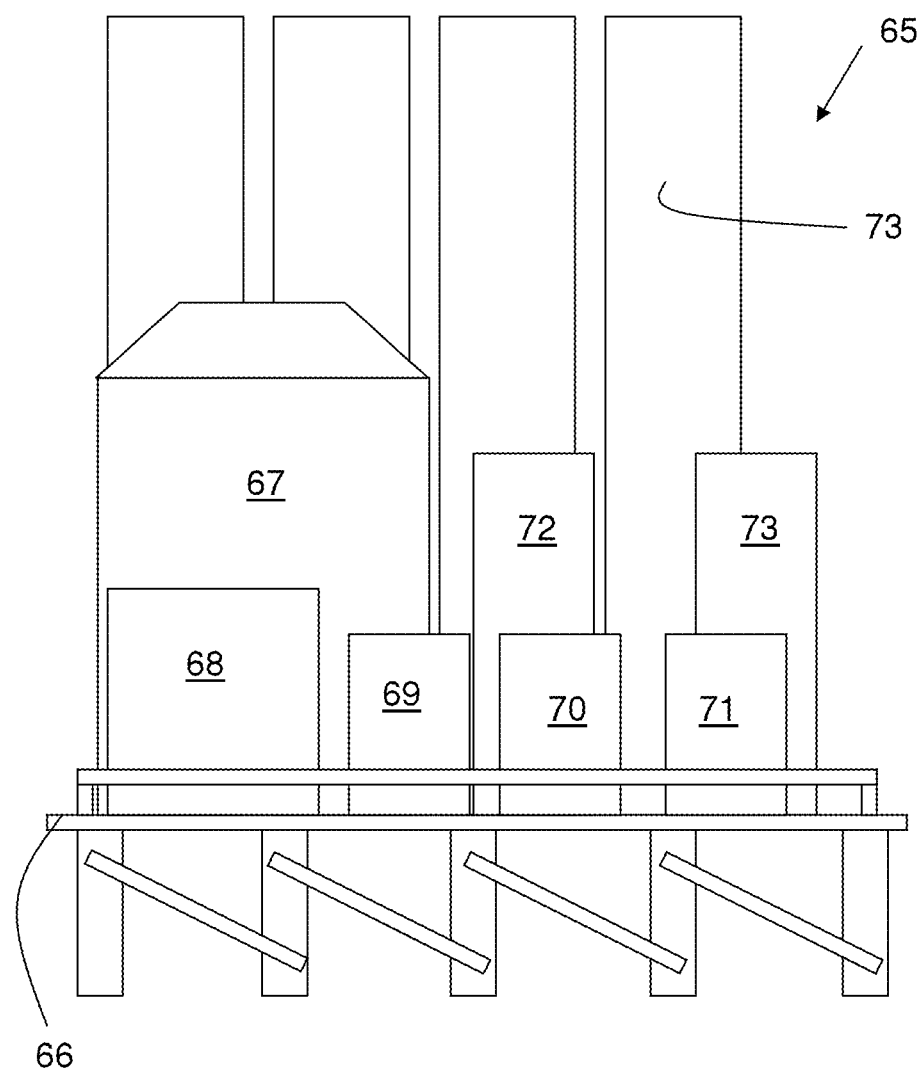
FIG. 3 depicts a side elevation view of a third embodiment of the microalgae-based soil inoculating system of the invention.

FIG. 3 depicts a side elevation view of another system (65) of the invention comprising an elevated portable platform (66), water tank (67), blower (68), ozone source (69), clarifier (70), water filter (71), nutrient source (72), carbon dioxide source (73). One or more components can be mounted on the platform and one or more components can be placed on the ground or onto one or more other platforms.

Although FIGS. 2 and 3 depict a water tank as the water supply, a flowing water source can be used instead; therefore, the system of the invention optionally includes one or more water tanks as the water supply or excludes a water tank as the water supply. Although not depicted in FIGS. 2 and 3, the effluent of one or more bioreactors can be fed into the water flow of an irrigation system. The systems of the invention can be placed within a partial or full enclosure even though the systems are portable.

Figure 4A:
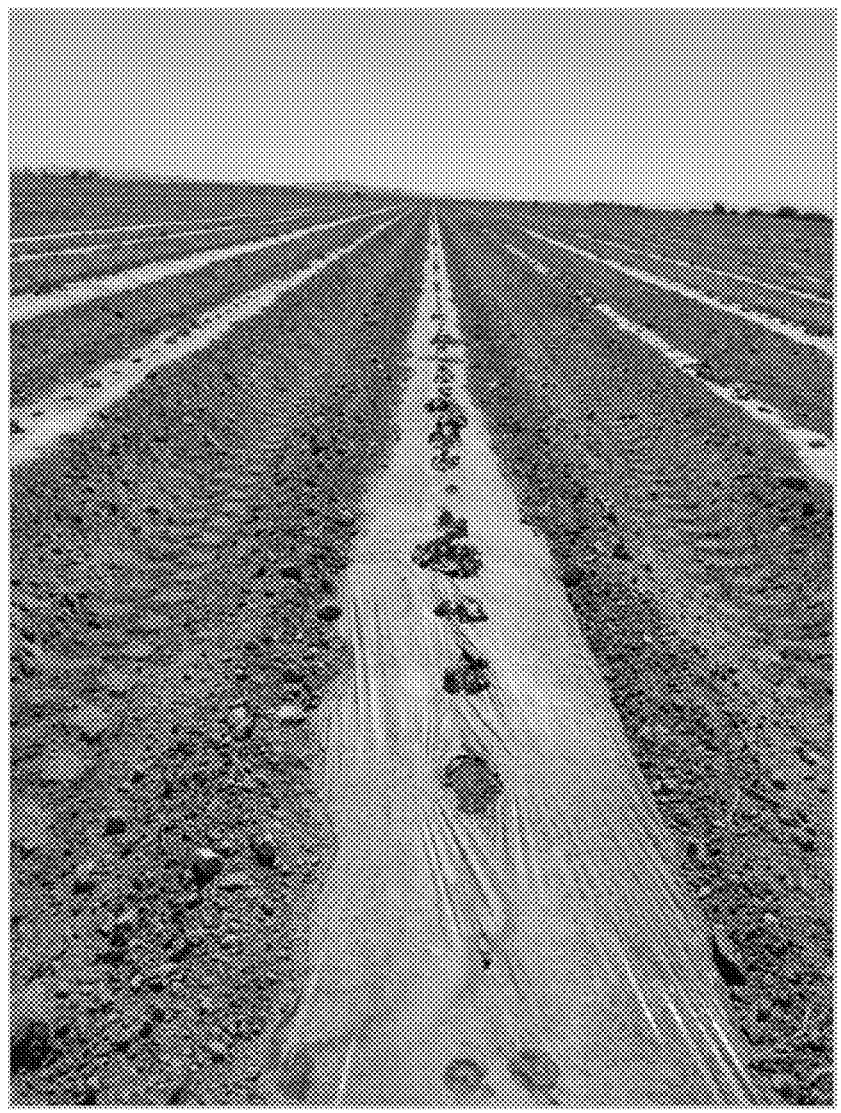
FIG. 4A depicts a field five weeks after a crop of melons was planted and treated according to the method and with the system of the invention.
Figure 4B:
FIG. 4B depicts the same field of FIG. 4A at nine weeks after a crop of melons was planted and treated according to the method and with the system of the invention.
Figure 5:
FIG. 5 depicts the same field of FIG. 4B, wherein strip sections of field (little plant growth) not treated according to the invention is compared to strip sections of field (lush plant growth) treated according to the invention.

The performance of the system of FIG. 2 was evaluated in a crop study wherein melon crops were planted in 200 acres of land. The land was divided into control and sample sections (FIG. 5). The control sections only received irrigation water and were not treated with microalgae supplement. The sample sections received only irrigation water containing the microalgae supplement. Melon seeds were planted before irrigating with the algae supplement in the soil. The control plants were irrigated about every fourth day, depending on the heat. The sample plants were irrigated on the same schedule as the controls. Various aspects of plant and fruit growth were evaluated five weeks (FIG. 4A) and nine weeks (FIG. 4B) after planting.

Figure 6A:
FIG. 6A depicts a melon plant in a section of field not treated according to the invention.
Figure 6B:
FIG. 6B depicts melon plants in a section of field treated according to the invention.
Figure 7A:
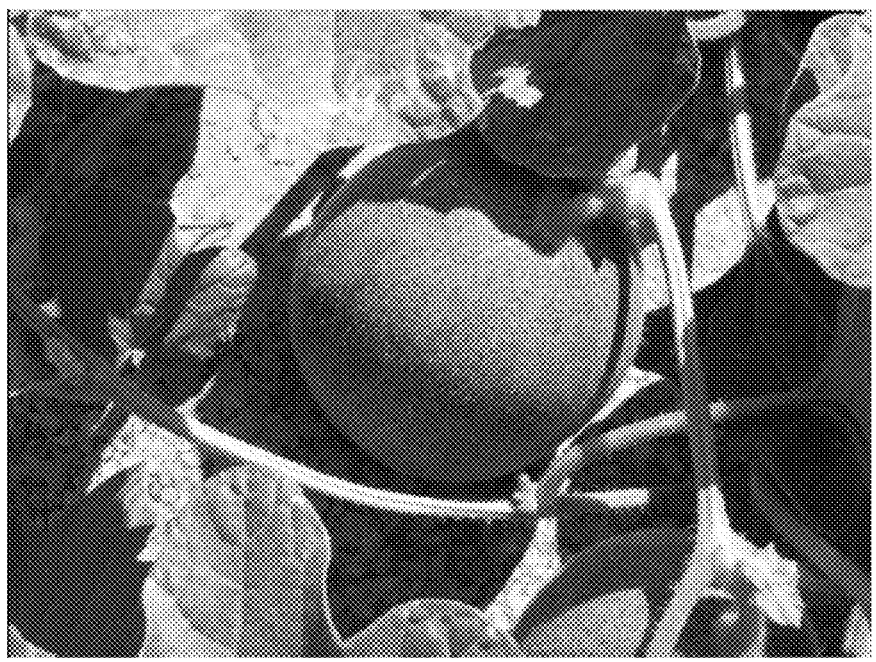
FIG. 7A depicts a melon growing in plant after nine weeks in a section of field not treated according to the invention.
Figure 7B:
FIG. 7B depicts a melon growing in plant after nine weeks in a section of field treated according to the invention.

Briefly, the crop grown according to the invention produced larger and hardier plants (compare FIG. 6A (control plant) to FIG. 6B (sample plant)), larger and tastier melons (compare FIG. 7A (control plant) to FIG. 7B (sample plant)). Moreover, the sample plants produced more flowers per vine, had improved fruit texture, improved sugar content, improved nutritional content, improved appearance, and improved Vitamin A content. The specific details and results are described in Example 1.

The system can further comprise one or more monitoring devices for performing functions such as measuring CO₂ flow rate, CO₂ content in the culture, O₂ content in the culture, pH, cell density and temperature in the culture, measuring macronutrient content in the culture or effluent, measuring micronutrient content in the culture or effluent, or measuring the microalgae titer in the culture or effluent.

Figure 8:
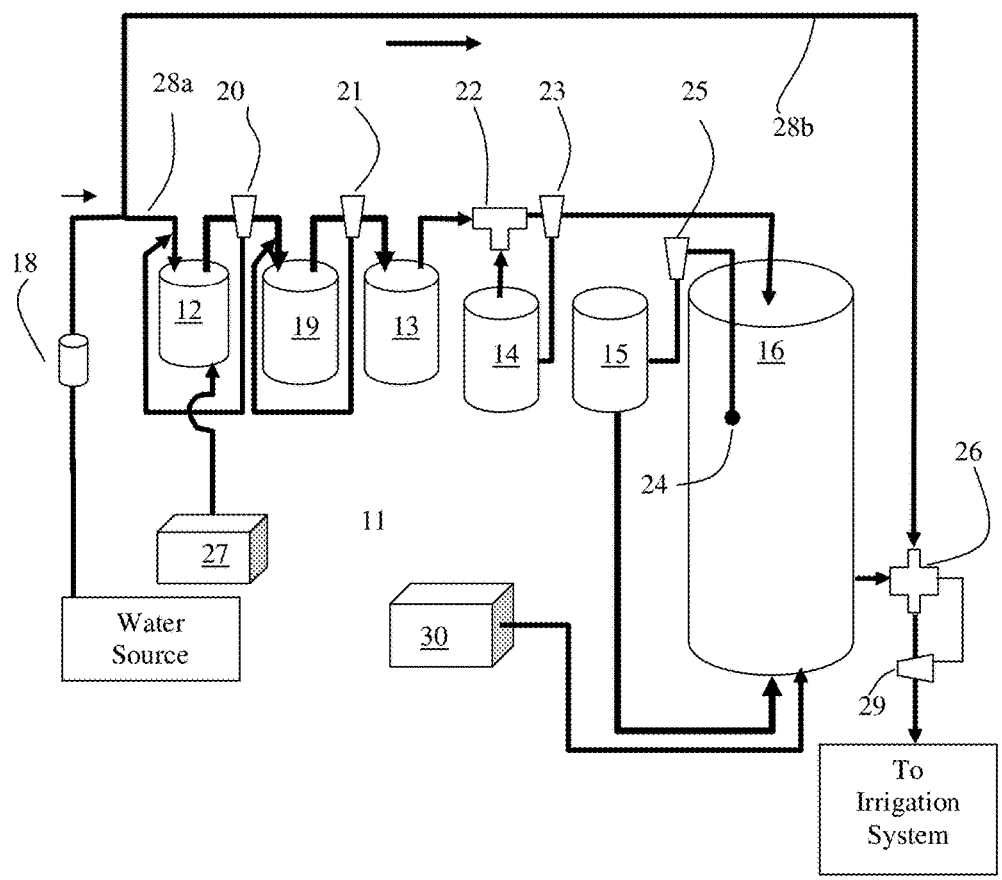
FIG. 8 depicts a fourth embodiment of the microalgae-based soil inoculating system of the invention.

FIG. 8 depicts an alternate embodiment of the system of the invention. This system (11) is suitable for low, medium and high volume irrigation applications. The system comprises an optional pump (18) adapted to receive water from a pressurized or unpressurized water source. The water is ozonated within an ozone contactor (12) that receives ozone from an ozone generator (27) and conducted to a clarifier/filter (19) that removes precipitated solids from the water. After clarification, the water is conducted to a carbon filter or UV light system (13), that removes the ozone, and through to a mixer (22) that mixes the water with algae feed material obtained from the algae feed supply (14). The algae/water mixture is mixed by use of air bubbles, which are produced by a blower (30), which conducts air to an air diffuser in the base of the bioreactor. The water containing nutrient material is conducted into the bioreactor (16), wherein microalgae are cultured. The effluent containing the microalgae exits the bioreactor and passes through a valve (26) that regulates the ratio of flow of water between the by-pass water source line (28b) and the bioreactor effluent. The controller (29) controls the valve (26) to achieve the desired ratio of volume of flow between untreated source water (from by-pass line 28b) and the effluent to provide an inoculant containing a desired or target microalgae titer.

The system (11) can include one or more different controllers. The controller (20) comprises an optional feedback loop such that water that has been improperly ozonated can be fed back into the ozone generator (12) for proper treatment. The controller (21) comprises an optional feedback loop such that water that has been insufficiently clarified can be fed back into the clarifier (19) for proper clarification. The controller (23) provides control over the algae nutrient supply (14) in order to regulate the amount of feed material that is charged into the water. The controller (25), by use of a pH probe (24), provides control over the carbon dioxide concentrator (15) that charges carbon dioxide into the bioreactor in order to regulate the concentration of carbon dioxide in the water and ensure the water has the proper carbon dioxide concentration. The system (11) can comprise a portable platform (or body or frame, not shown) onto which plural components of the system are mounted. Each of the individual components of the system is individually replaceable. Although the components are indicated as single components, each of the components can be present in plurality independently of other components of the system.

Figure 9:
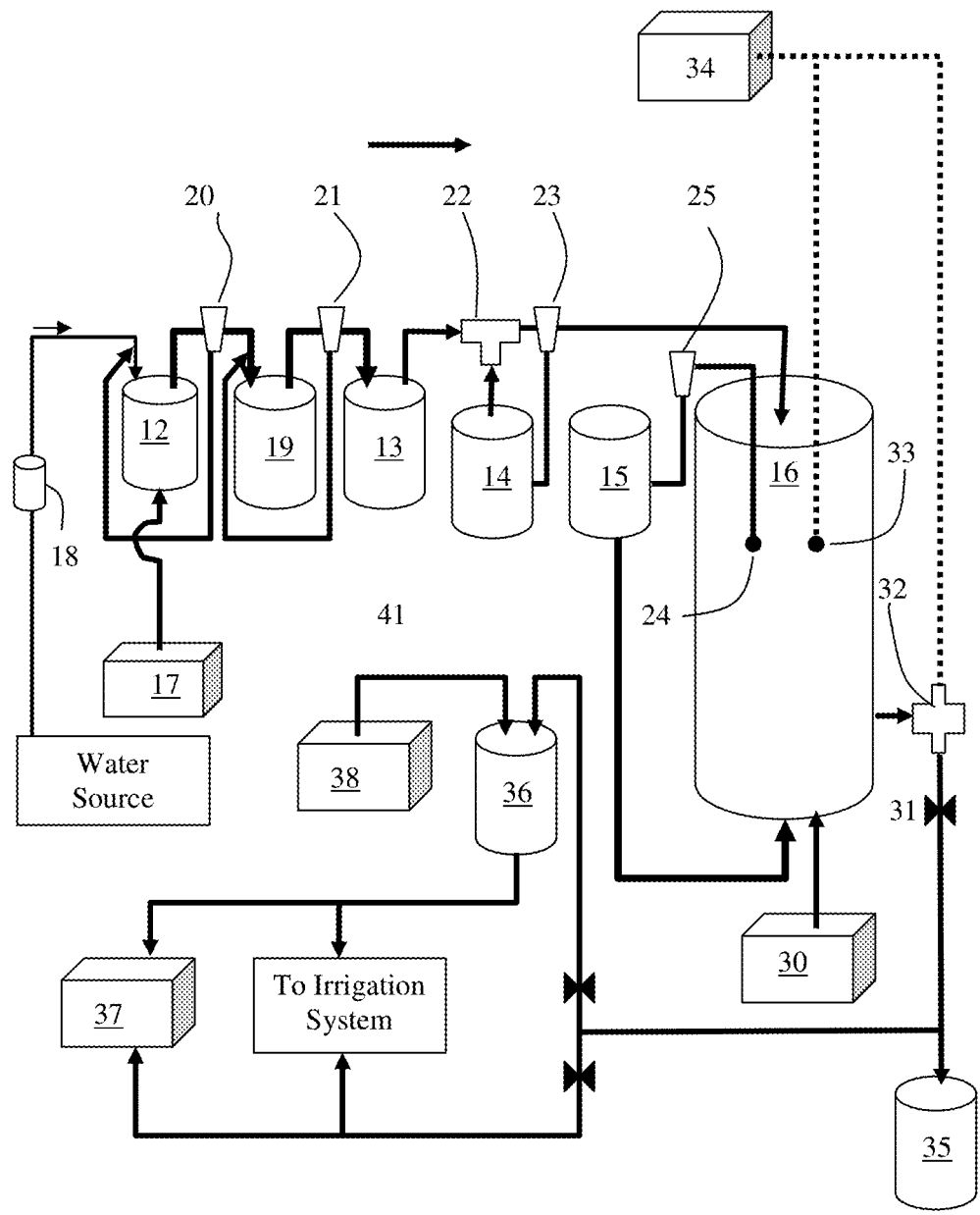
FIG. 9 depicts a fifth embodiment of the microalgae-based soil inoculating system of the invention.

FIG. 9 depicts an alternate embodiment (41) of the system of the invention. This alternate embodiment of the system is suitable for low, medium and high volume irrigation applications or flowing to a distribution tank or 5 gallon carboys (37). The tank may sit on a trailer for portability. The system comprises an optional pump (18) adapted to receive water from a pressurized or unpressurized water source. The water is ozonated within an ozone contactor (12) that receives ozone from an ozone generator (17). The ozonated water is conducted to a clarifier/filter (19) that removes precipitated solids from the water. After clarification, the water is conducted to a carbon filter or UV light system (13), that removes the ozone, and through to a mixer (22) that mixes the water with algae fertilizer/additives obtained from the algae fertilizer/additive supply (14). The water containing nutrient material is conducted into the bioreactor (16), wherein microalgae are cultured. The algae/water mixture is mixed by use of air bubbles, which are produced by a blower (30), which conducts air to an air diffuser in the base of the bioreactor. Probes (33) in the culture measure the critical parameters including pH, temperature, cell density, water mixing velocity, dissolved gasses and proteins, An optional telemetry device (34) sends the metrics from the probes (monitoring devices or controllers) to a computer server for remote monitoring. An optional telemetry capable microscope assists remote culture monitoring.

As used herein, a telemetry device is any device capable of facilitating communication between the system of the invention and a communications and/or control center remote from or at a different geographic locale than the system of the invention. A telemetry device can employ any type of wireless communication system and can employ any frequency of light waves, radio waves, sound waves, infrared waves, hypersonic waves, ultraviolet waves, other such wavelengths/frequencies and combinations thereof. It can also employ an IP network (such as the Internet), GSM (global system for mobile communications) network, SMS (short message service) network, other such systems and combinations thereof.

A Flow Imaging device (32) creates images of the algae, predators and contaminants in the culture for QC (quality control) purposes and sends this data to the telemetry device. The effluent containing the microalgae exits the bioreactor and passes through a valve (31) that regulates the flow of the bioreactor effluent. An optional dewatering device (35) can concentrate the algae into slurry of the desired density, which may flow to irrigation or portable containers (37). An optional microorganism mixer (36) enables the user to blend the final product with, in addition to algae, beneficial bacteria, viruses, fungi, slimes or other organisms (38) that work symbiotically with algae.

The system can include one or more different controllers. The controller (20) comprises an optional feedback loop such that water that has been improperly ozonated can be fed back into the ozone generator (12) for proper treatment. The controller (21) comprises an optional feedback loop such that water that has been insufficiently clarified can be fed back into the clarifier (19) for proper clarification. The controller (23) provides control over the algae nutrient supply (14) in order to regulate the amount of feed material that is charged into the water. The controller (25) by use of a pH probe (24) provides control over the carbon dioxide concentrator (15) that charges carbon dioxide into the bioreactor in order to regulate the concentration of carbon dioxide in the water and ensure the water has the proper carbon dioxide concentration. The system (11) can comprise a portable platform (or body or frame, not shown) onto which plural components of the system are mounted. Each of the individual components of the system is individually replaceable. Although the components are indicated as single components, each of the components can be present in plurality independently of other components of the system.

A system similar to FIG. 9 can be used to reclaim degraded or abandoned soil. The algae and microorganism mixture may be applied though irrigation or spaying on the soil surface to restore vital nutrients. Algae and the other microorganisms continue to flourish in the soil as long as soil moisture is available. Algae deliver micronutrients, attract other microorganisms and add organic matter (humus) to the soil. The process can rehabilitate degraded or abandoned soil.

A system similar to FIG. 9 can culture other microorganisms in the same culture or separate containers for blending before the culture flows into the irrigation or portable containers.

In view of the above description and the examples below, one of ordinary skill in the art will be able to practice the invention as claimed without undue experimentation. The foregoing will be better understood with reference to the following examples. All references made to these examples are for the purposes of illustration. The following examples should not be considered exhaustive, but merely illustrative of only a few of the many embodiments contemplated by the present invention.

Example 1

Evaluation of the System for Melon Growth

The system of the invention was used to grow the Yosemite variety of cantaloupe melons. About 200 acres were infused with microalgae-containing irrigation water. The crop was watered every five days during afternoons due to high ambient temperatures (120° F.). Microalgae were added to the irrigation water continuously with each watering. Algae from the class Chlorophyceae and cyanobacteria were added to the irrigation water at a combined density of 6 billion cells per minute. The algae were cultured in media shown in the table below.

| FW Media | | | |
|---|---|---|---|
| | Final Conc. (g/L) | Stock Solutions (g/L) | Use Rate (ml/L) |
| N & P Solution | | | |
| $NaNO_3$ | 0.344 | 34.4 | 10 |
| KCl | 0.303 | 30.3 | |
| $NaH_2PO_4$ | 0.03 | 2.91 | |
| Missing element solutions | | | |
| $CaCl_2-2H_2O$ | 0.11 | 11 | 10 |
| $MgSO_4 \cdot 7H_2O$ | 0.246 | 24.6 | |
| Trace Element Solution | | | |
| $Na_2EDTA-2H_2O$ | 0.0045 | 4.5000 | 1 |
| $FeCl_3 \cdot 6H_2O$ | 0.00289 | 2.8910 | |
| $MnCl_2-4H_2O$ | 0.00098 | 0.9800 | |
| $ZnSO_4 \cdot 7H_2O$ | 0.000036 | 0.0360 | |
| $CoCl_2 \cdot 6H_2O$ | 0.000011 | 0.0110 | |
| $Na_2MoO_4-2H_2O$ | 0.00012 | 0.1200 | |
| $CrO_3$ | 0.000075 | 0.0750 | |
| $SeO_2$ | 0.000005 | 0.0050 | |
| $CuSO_4 \cdot 5H_2O$ | 0.000012 | 0.0120 | |
| Vitamins | | | |
| Biotin | 0.000025 | 0.025 | 1 |
| Thiamine HCl | 0.0000175 | 0.017 | |
| B12 | 0.000015 | 0.015 | |

The melons were harvested and the following observations were made when comparing melons grown according to the invention to melons not grown according to the invention.

| Metric | Description |
| --- | --- |
| Productivity | Improved melon production 20% by weight. |
| Size | Fruit increased in diameter by 22%. |
| Texture | Texture of meat of the fruit held or improved. |
| Shelf-life | The shelf-life was extended by 4 days. |
| Taste | Taste of the fruit held or improved. |
| Sugar | Sweetness of the fruit improved by 20%. |
| Appearance | Appearance, color, of the fruit held or improved. |
| Vitamin A | Vitamin content improved by 20%. |

Various different dimensions of the melon plants were measured at 9-weeks after planting both for control plants and plants grown with the system of the invention. The observed dimensions are detailed below.

| Parameter | Control | Sample | Fold increase |
| --- | --- | --- | --- |
| Trunk Diameter | 0.129 in | 0.38 in | 2.9 |
| Stem diameter | 0.05 in | 0.125 in | 2.5 |
| Average Leaf length | 2.5 in | 4 in | 1.6 |
| Largest Leaf length | 3.5 in | 7 in | 2.0 |
| Overall plant radius | 37.8 in | 87.12 in | 2.3 |
| Overall plant height | 5.7 in | 15 in | 2.6 |
| Flower size width | 0.9 in | 2.3 in | 2.6 |
| Melon diameter | 2.3 in | 5.5 in | 2.4 |

The algae infused melon fields required 50% less N inorganic fertilizer and 40% less P and K. Micronutrient savings were on the order of 70%. The farmer reported a 5-fold improvement in soil porosity, looseness, which enabled deeper crop roots. Higher soil porosity also enabled symbiotic macro and microorganisms to enter the field such as earthworms. The farmer reported that the melon fields needed over 50% less pesticide application, because the algae infused crops seemed to make their own biopesticides that discouraged invaders, such as white flies that destroyed neighboring fields. The farmer used 70% less fungicide as the algae enabled longer roots that were more resistant to nematodes and other soil pests. Accordingly, the system of the invention provides substantial improvements in characteristics of plants and fruits grown with the system of the invention.

Example 2

Evaluation of the System for Other Crop Growth

Tomatoes
Tomatoes grown in a hot house in soil infused with microalgae. Their growth was compared to a control crop of tomatoes, which soil was not infused with microalgae. The treated tomatoes exhibited faster growth with larger, juicier, redder produce, lower acid content, improved flavor as compared to untreated control tomatoes. They also exhibited an average of ten days to two weeks earlier maturing rate, a significant resistance to disease (principally the mosaic virus), and increases in yields of 10-23% in certain varieties.
Corn
Algae biofertilizer, fossilized algae from mines of ancient oceans, was applied to a crop of corn grown on a field. The corn exhibited increased germination rates, increased ear and kernel size, increased protein content, earlier maturation, and increased yields both in silage crops and feed corn as compared to untreated control corn. The microalgae also increased the crop's ability to withstand disease and insect infestation and increased the sugar content of the corn milk.
Soybeans
Soybeans grown in soil inoculated with cyanobacteria exhibited an increase of 22% in the germination rate on 32 different experiments, 29% more nodulation in the rhizosphere, 21% yield increase, 9% protein increase, better disease resistance, lower requirements and earlier crop maturation as compared to untreated control soybeans.
Cotton
Biofertilizers in cyanobacteria, blue-green algae, as well as green algae were used to inoculate soil having cotton growing therein. The treated cotton exhibited increased germination and growth rates, more blossoms, more squares, heavier setting of fruit with less loss dropping from the blossom to square to boll setting, sturdier stems and stocks and heavier setting of seeds in the boll as compared to untreated control cotton. The luster of the cotton fiber increased, which improved the grade and the price. Biofertilized cotton plants had lower nitrogen requirements, lower water requirements, higher yields per acre and increased disease resistance as compared to cotton plants not treated with the microalgae.

Example 3

Crop Growth Employing Two Different Microalgae

Prior to planting the seeds of a crop in soil, the soil is irrigated repeatedly with an inoculate containing a first species from the phylum Chlorophycophyta of microalgae until the soil has achieved the desired properties of increased organics with polysaccharides in the soil to increase water retention Seeds are planted in the treated soil and irrigated repeatedly with an inoculate containing a different second species from the phylum Cyanophycophyta of microalgae to infuse the soil with nitrogen sequestered from the atmosphere. until the crop has reached maturity. The crop is then harvested using known methods. At his point a third species also from the phylum Cyanophycophyta is introduced into the irrigation water and delivered to the soil where it produces a biological toxin to kill unwanted pests in the soil. The first species of the phylum Chlorophycophyta of microalgae is used to enhance the fertility and other properties of the soil by increasing the organics in the soil which enhances the colonization by other micro and macro organisms which further enhance the soil by converting nutrients into forms more available to the crop and by increasing the porosity of the soil. The second species from the phylum Cyanophycophyta of microalgae is used to add nitrogen to the soil thereby reducing the amount of nitrogen fertilizer needed by the crop. The third species from the phylum Cyanophycophyta is used to eliminate or reduce the amount of pests in the soil.

Example 4

System Employing Co-Culture of Two Different Microalgae

A system containing a co-culture of two different microalgae strains are prepared by preparing a culture medium in one or more bioreactors and inoculating it with one or more blue-green algae (cyanobacteria or cyanophyta) and one or more green algae (chlorophyta). Both algae can be independently unicellular or colonial; however, unicellular species are preferred. Exemplary chlorophyta include those of the class chlorophyceae, which includes those of the order Chaetopeltidales, Chaetophorales, Chlamydomonadales, Chlorococcales, Chlorocystidales, Dunaliella, Microsporales, Oedogoniales, Phaeophilales, Sphaeropleales, Tetrasporales or Volvocales. Exemplary chlorophyta species include *Chlorella fusca, Chlorella zofingiensis, Chlorella* spp., *Chlorococcum citriforme, Chlorella stigmataphora, Chlorella vulgaris, Chlorella pyrenoidosa* and others. Exemplary cyanophyta include those of the phyla Chroococcales, Gloeobaterales, Nostocales, Oscillatoriales, Pseudanabaenales, and Synechococcales. The algae are co-cultured with natural and/or artificial light. The titer of algae in the culture medium is allowed to increase to a target level of about 1 MM to 10 MM or 1 MM to 100 MM cells per ml. The culture medium is discharged from the bioreactor and mixed in with water for irrigation to provide an inoculate having a titer of algae in the culture medium of about 1 MM to 10 MM cells per ml.

As used herein and unless otherwise specified, the term "about" or "approximately" are taken to mean±10%, ±5%, ±2.5% or ±1% of a specified valued. As used herein and unless otherwise specified, the term "substantially" is taken to mean "to a large degree", "at least a majority of", greater than 70%, greater than 85%, greater than 90%, greater than 95%, greater than 98% or greater than 99%.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

What is claimed is:

1. A microalgae-based soil inoculating system for inoculation of water from a water source with microalgae, wherein the system comprises:
    an ozone contactor configured to receive an incoming water supply from the water source;
    an ozone generator coupled to the ozone contactor, wherein the ozone generator generates ozone and delivers the ozone to the incoming water in the ozone contactor and forms ozone-treated water;
    a solids filter immediately downstream to an outlet of the ozone contactor, wherein the solids filter removes solids from the ozone-treated water;
    at least one of a carbon filter and a UV light system positioned immediately downstream from the solids filter, wherein the at least one of the carbon filter and the UV light system removes ozone from the ozone-treated water and forms deozonated water;
    a bioreactor positioned downstream of the at least one of the carbon filter and the UV light system, wherein the bioreactor:
        receives and contains:
            the deozonated water from the at least one of the carbon filter and the UV light system; and
            the microalgae;
        cultivates a suspension culture of the microalgae in the deozonated water and forms a microalgae-containing inoculant effluent having a microalgae cell concentration of at least about 1,000,000 cells per milliliter; and
        exposes the microalgae-containing inoculant effluent to at least one of natural and artificial light;
    a blower coupled to the bioreactor, wherein the blower:
        aerates the microalgae-containing inoculant effluent; and
        agitates the microalgae-containing inoculant effluent and mixes the microalgae with the deozonated water; and
    a carbon dioxide source coupled to the bioreactor, wherein the carbon dioxide source adds carbon dioxide to the microalgae-containing inoculant effluent.

2. The system of claim 1, wherein the water source comprises at least one water supply.

3. The system of claim 2, wherein the water supply comprises at least one water reservoir or at least one tank adapted to temporarily hold water.

4. The system of claim 1, wherein at least one of the solids filter, the carbon filter, the UV light system, and the bioreactor is a flow-through apparatus coupled through one or more water conduits.

5. The system of claim 1, wherein the system comprises at least two different microalgae species.

6. The system of claim 1, further comprising a microalgae-nutrient feed source comprising at least one of a fertilizer, a macro-nutrient, and a micro-nutrient.

7. The system of claim 6, wherein the macro-nutrients are selected from the group consisting of phosphorus, nitrogen, carbon, silicon, calcium salt, magnesium salt, sodium salt, potassium salt, and sulfur; and the one or more micronutrients is selected from the group consisting of manganese, copper, zinc, cobalt, molybdenum, vitamins and trace elements.

8. The system according to claim 1, wherein the system is communicatively linked to a telemetry system for at least one of remote monitoring and controlling the operation of one or more of: the ozone source, the solids filter, the at least one of the carbon filter and the UV light system, the bioreactor, the blower, and the carbon dioxide source.

9. The system of claim 1, wherein the system further comprises at least one water conduit connecting at least one of the water source, the ozone contactor, the solids filter, the at least one of the carbon filter and the UV filter, and the bioreactor.

10. The system of claim 9, wherein the system further comprises a pump fluidly coupled to the water source and pumping water through the at least one water conduit.

11. The system of claim 1, further comprising a light source comprising LED lights, wherein the light source is positioned at least one of within the bioreactor and proximate to an exterior surface of the bioreactor and exposing the microalgae to light.

12. The system of claim 1, wherein the ozone generator uses at least one of dry air and 90% oxygen from an oxygen concentrator and generates the ozone.

13. The system of claim 1, wherein the carbon dioxide source comprises at least one of a tank containing carbon dioxide gas, a carbon dioxide generator, and a carbon dioxide-sequester that sequesters and temporarily stores atmospheric carbon dioxide.

14. The system of claim 1, wherein the bioreactor receives and contains at least one of a second algae, a bacteria, a fungi, a nematode, and a protozoa.

15. The system of claim 1, further comprising a pH meter coupled to the bioreactor and measuring the pH of the microalgae-containing inoculant effluent.

16. The system of claim 1, wherein a micronutrient solution comprising at least one of a vitamin and a mineral is added to the deozonated water.

17. A method of growing a crop using an irrigation-water supply from a water source, comprising:

conducting the irrigation-water supply through a microalgae-based soil inoculating system, wherein the microalgae-based soil inoculating system comprises:
  an ozone contactor coupled to an ozone generator, wherein:
    the ozone contactor receives the irrigation-water supply from the water source; and
    the ozone generator generates ozone and delivers the ozone to the irrigation-water supply and forms ozone-treated water;
  a solids filter immediately downstream of an outlet of the ozone contactor and removing solids from the ozone-treated water;
  at least one of a carbon filter and a UV light system positioned immediately downstream from the solids filter, wherein the at least one of the carbon filter and the UV light system removes ozone from the ozone-treated water and forms deozonated water;
  a bioreactor positioned downstream of the at least one of the carbon filter and the UV light system, wherein the bioreactor:
    receives and contains:
      the deozonated water from the at least one of the carbon filter and the UV light system; and
      the microalgae;
    cultivates a suspension culture of the microalgae in the deozonated water and forms a microalgae-containing inoculant effluent having a microalgae cell concentration of at least about 1,000,000 cells per milliliter; and
    exposes the microalgae-containing inoculant effluent to at least one of natural and artificial light;
  a blower coupled to the bioreactor, wherein the blower:

aerates the microalgae-containing inoculant effluent; and agitates the microalgae-containing inoculant effluent and mixes the microalgae with the deozonated water; and a carbon dioxide source coupled to the bioreactor, wherein the carbon dioxide source adds carbon dioxide to the microalgae-containing inoculant effluent; and irrigating the crop one or more times with the microalgae-containing inoculant effluent.

18. The method according to claim 17 wherein the soil is treated with the microalgae-containing inoculant effluent daily, every other day, every third day, semi-weekly, every fourth day, every fifth day, every sixth day, weekly, biweekly, every third week, every fourth week, monthly, bimonthly, quarterly, trimesterly, semiannually, annually or a combination thereof.

19. The method according to claim 17, further comprising at least one of:

a) alternating treatment of the soil with untreated irrigation-water from the water source and the microalgae-containing inoculant effluent;

b) diluting the microalgae-containing inoculant effluent to form a semi-concentrated microalgae-containing inoculant effluent prior to irrigating the crop; and a) adding a second species of microalgae.

20. The method of claim 17, wherein the microalgae-based soil inoculating system further comprises a distribution tank connected to an outlet of the bioreactor and configured to receive the microalgae-containing inoculant effluent from the bioreactor and wherein the crop is irrigated one or more times with the microalgae-containing inoculant effluent from the distribution tank.

21. A microalgae-based soil inoculating system for inoculation of water from a water source with a microalgae, wherein the system comprises:

an ozone contactor, wherein the ozone contactor receives and holds an amount of the water from the water source;

an ozone generator connected immediately downstream to the ozone contactor, wherein the ozone generator generates ozone and delivers the ozone to the water in the ozone contactor and forms ozone-treated water;

a solids filter immediately downstream to an outlet of the ozone contactor, wherein the solids filter:

receives the ozone-treated water from the ozone contactor; and removes solids from the ozone-treated water to form a filtered water;

a UV light system positioned immediately downstream of the solids filter, wherein the UV light system:

receives the filtered water from the solids filter; and removes ozone from the filtered water and forms deozonated water;

a bioreactor positioned downstream of the UV light, wherein the bioreactor:

receives and contains:

the deozonated water from the UV light system; and the microalgae;

cultivates a suspension culture of the microalgae in the deozonated water and forms a microalgae-containing inoculant effluent having a microalgae cell concentration of at least about 1,000,000 cells per milliliter; and exposes the microalgae-containing inoculant effluent to at least one of natural and artificial light;

a light source positioned at least one of within the bioreactor and proximate to an exterior surface of the bioreactor, wherein the light source directs artificial light onto the microalgae-containing inoculant effluent;

a blower coupled to the bioreactor, wherein the blower:

aerates the microalgae-containing inoculant effluent; and agitates the microalgae-containing inoculant effluent and mixes the microalgae with the deozonated water; and a carbon dioxide source coupled to the bioreactor, wherein the carbon dioxide source adds carbon dioxide to the microalgae-containing inoculant effluent;

a water pump, wherein the water pump circulates at least one of the water and the filtered water downstream towards the bioreactor; and a distribution tank coupled to an outlet of the bioreactor, wherein the distribution tank receives the microalgae-containing inoculant effluent from the bioreactor.

22. The system of claim 21, further comprising a second species of microalgae.

23. The system of claim 21, wherein the bioreactor comprises at least one light-permeable wall.

24. The system of claim 21, further comprising a portable body onto which the microalgae-based soil inoculating system is mounted.

25. The system of claim 21, further comprising at least one water conduit and a cleaning system, wherein the cleaning system is configured to clean at least one of the water conduit and the bioreactor.

26. The system of claim 21, further comprising at least one monitor connected to the bioreactor and configured to at least one of monitor the growth conditions in the bioreactor, assess microalgae cell titer in the bioreactor, monitor the pH of the microalgae-containing inoculant effluent in the bioreactor, monitor the salinity of the water, detect contaminating organisms, monitor water pressure, monitor the clarity of the filtered water, image the microalgae-containing inoculant effluent, and control the concentration of at least one of ozone, carbon dioxide, nitrogen, and oxygen in the water.

27. The system according to claim 26, wherein the system is communicatively linked to a telemetry system for at least one of remote monitoring and controlling the operation of at least one of: the ozone source, the UV light system, the bioreactor, the light source, the water pump, the blower, the carbon dioxide source, and the distribution tank.

28. The system of claim 21, wherein the system further comprises at least one water conduit connecting at least one of the water source, the solids filter, the at least one of the carbon filter and the UV filter, the bioreactor, and the distribution tank.

* * * * *